US009285961B2

United States Patent
Jo et al.

(10) Patent No.: US 9,285,961 B2
(45) Date of Patent: Mar. 15, 2016

(54) ULTRASONIC DIAGNOSIS DEVICE, GRAPHIC ENVIRONMENT CONTROL DEVICE FOR USE THEREIN, AND CONTROL METHOD THEREFOR

(75) Inventors: Dong Min Jo, Seoul (KR); Jin Yong Park, Seoul (KR)

(73) Assignee: ALPINION MEDICAL SYSTEMS CO., LTD. (KR)

( * ) Notice: Subject to any disclaimer, the term of this patent is extended or adjusted under 35 U.S.C. 154(b) by 0 days.

(21) Appl. No.: 13/704,536

(22) PCT Filed: May 23, 2011

(86) PCT No.: PCT/KR2011/003763
§ 371 (c)(1),
(2), (4) Date: Dec. 14, 2012

(87) PCT Pub. No.: WO2011/159033
PCT Pub. Date: Dec. 22, 2011

(65) Prior Publication Data
US 2013/0090558 A1 Apr. 11, 2013

(30) Foreign Application Priority Data
Jun. 14, 2010 (KR) .................. 10-2010-0055906

(51) Int. Cl.
*A61B 8/00* (2006.01)
*G06F 3/0484* (2013.01)

(52) U.S. Cl.
CPC ............ *G06F 3/0484* (2013.01); *A61B 8/4405* (2013.01); *A61B 8/464* (2013.01); *A61B 8/465* (2013.01); *A61B 8/467* (2013.01); *A61B 8/461* (2013.01)

(58) Field of Classification Search
CPC .... G06F 3/0484; A61B 8/4405; A61B 8/461; A61B 8/467; A61B 8/464; A61B 8/465
USPC .................................................. 600/437–469
See application file for complete search history.

(56) References Cited

U.S. PATENT DOCUMENTS 5,111,823 A 5/1992 Cohen
5,299,577 A 4/1994 Brown et al.
(Continued)

FOREIGN PATENT DOCUMENTS

EP 2 110 764 A1 10/2009
JP 2801396 B2 7/1998
(Continued)

OTHER PUBLICATIONS

International Search Report (in Korean and English) for PCT/KR2011/003763, mailed Dec. 23, 2011; ISA/KR.

*Primary Examiner* — Sanjay Cattungal
(74) *Attorney, Agent, or Firm* — Harness, Dickey & Pierce, P.L.C.

(57) ABSTRACT

An ultrasonic diagnostic apparatus, a graphic environment control device for use therein, and a control method therefor are provided. The ultrasonic diagnostic apparatus includes: a touch panel for detecting an operator's touch position; a display for displaying images in response to ultrasonic waves radiated from a probe and reflections of the ultrasonic waves; and a graphic control unit for displaying an input panel layout corresponding to the touch panel on the display, selecting a position on the input panel layout corresponding to a touch position detected by the touch panel, and performing a control operation corresponding to the position selected on the input panel layout.

11 Claims, 6 Drawing Sheets

(56) References Cited

U.S. PATENT DOCUMENTS

| | | | |
|---|---|---|---|
| 5,383,457 A | 1/1995 | Cohen | |
| 6,135,958 A * | 10/2000 | Mikula-Curtis et al. | 600/443 |
| 6,491,630 B1 * | 12/2002 | Saccardo et al. | 600/437 |
| 8,517,946 B2 * | 8/2013 | Kim | 600/443 |
| 2007/0162869 A1 * | 7/2007 | Watanabe et al. | 715/808 |
| 2010/0145195 A1 * | 6/2010 | Hyun | 600/437 |
| 2010/0179427 A1 * | 7/2010 | Yamamoto | 600/443 |
| 2011/0208052 A1 * | 8/2011 | Entrekin | 600/437 |
| 2012/0092334 A1 | 4/2012 | Yoo | |
| 2012/0110447 A1 * | 5/2012 | Chen | 715/702 |
| 2012/0116225 A1 | 5/2012 | Kim | |
| 2012/0123269 A1 | 5/2012 | Roh et al. | |
| 2012/0204416 A1 | 8/2012 | Bae et al. | |
| 2012/0313879 A1 * | 12/2012 | Harrison | 345/173 |
| 2013/0253323 A1 * | 9/2013 | Kim | 600/443 |
| 2013/0296702 A1 * | 11/2013 | Chang et al. | 600/440 |

FOREIGN PATENT DOCUMENTS

| | | |
|---|---|---|
| JP | 2005-253693 A | 9/2005 |
| KR | 10-2010-0047391 A | 5/2010 |

* cited by examiner

ULTRASONIC DIAGNOSIS DEVICE, GRAPHIC ENVIRONMENT CONTROL DEVICE FOR USE THEREIN, AND CONTROL METHOD THEREFOR

TECHNICAL FIELD

The present disclosure relates in some embodiments to an ultrasonic diagnostic apparatus, a graphic environment control device for use therein and a control method therefor. More particularly, the present disclosure relates to an ultrasonic diagnostic apparatus, a graphic environment control device for use therein and a control method therefor, wherein an operator is relieved from the need to move arm positions between the control panel and touch screen for each manipulation of the ultrasonic diagnostic apparatus as well as the need for constant visual attention switches between the touch screen and display.

BACKGROUND

The statements in this section merely provide background information related to the present disclosure and may not constitute prior art.

An ultrasonic diagnostic equipment or ultrasonic diagnostic apparatus is a type of an inspection apparatus that irradiates ultrasonic wave on an inspection site of an object (for example, human body), detects a time difference between the irradiated ultrasonic wave and rebound echo reflected from the interior of the object, converts the detected time difference to a distance by using an electronic circuit, and images the inspection site of the object. The ultrasonic wave used in the ultrasonic diagnostic apparatus is harmless to humans. Therefore, the ultrasonic diagnostic apparatus is particularly useful for medical purposes and is widely used for detection of foreign substance inside human body, determination of the degree of damage, and monitoring a tumor or fetus.

FIG. 1 is a diagram for showing one example of a conventional ultrasonic diagnostic apparatus. Referring to FIG. 1, an ultrasonic diagnostic apparatus 100 is typically implemented in a transportable construction and includes a body 110, a control panel 120 and a display 130. The body 110 is mounted with an electronic circuit and a module for executing various control functions. The control panel 120 is provided with an input device, such as a keyboard, a switch, and a track ball, to allow an operator to input commands required for ultrasonic diagnosis. The display 130 performs signal processing on an ultrasonic wave irradiated through a probe and an echo, and displays the resultant image.

On the other hand, as digital electronic technologies have recently developed, the functions and inspection capability of ultrasonic diagnostic apparatuses have greatly enhanced. In order to sufficiently utilize such enhanced functions, it became necessary to extend an input device used and manipulated by an operator. However, there is a limitation to extending the control panel 120 alone by way of hardware, and a new function for separate manipulation guidance became necessary so as to allow an operator to appropriately manipulate a complicated input device.

For this purpose, a touch screen 140 is provided for displaying additional graphic environment for manipulation and input of the operator independently of the display 130, and guiding an operator to appropriately manipulate an input device and input commands for different situations.

Generally, as shown in FIG. 1, the touch screen 140 is installed between the control panel 120 and the display 130. The touch screen 140 also serves to execute a screen function of displaying graphic environment for input and manipulation of an operator as well as a touch panel function of recognizing an operator touch point corresponsive to the displayed graphic environment and executing an additional function and a control operation.

Since the touch screen 140 is typically implemented with a liquid crystal display (LCD) for displaying the graphic environment, it needs to maintain a predetermined tilt angle as shown in FIG. 2, considering the angle of the line of sight of the operator. Therefore, the control panel 120 and touch screen 140 inevitably have different installation angles from each other. However, in many cases, the control panel 120 and the touch screen 140 are alternately operated in order for the user to manipulate the ultrasonic diagnostic apparatus 100. Therefore, the operator needs to move arm positions for each manipulation of the ultrasonic diagnostic apparatus 100.

In addition, since the display 130 and the touch screen 140 of the conventional ultrasonic diagnostic apparatus 100 are located at different positions, the operator needs to alternately switch visual attention between the display 130 and touch screen 140 in the manipulation of the ultrasonic diagnostic apparatus 100.

DISCLOSURE

Technical Problem

Therefore, the present disclosure is directed to providing an ultrasonic diagnostic apparatus, a graphic environment control device for use therein and a control method therefor, wherein an operator is relieved from the need to move arm positions between the control panel and touch screen for each manipulation of the ultrasonic diagnostic apparatus as well as the need for constant visual attention switches between the touch screen and display.

SUMMARY

An embodiment of the present disclosure provides an ultrasonic diagnostic apparatus including: a touch panel for detecting a touch position; a display for displaying images in response to ultrasonic waves radiated from a probe and reflections of the ultrasonic waves; and a graphic control unit for displaying an input panel layout corresponding to the touch panel on the display, selecting a position on the input panel layout corresponding to the touch position detected by the touch panel, and performing a control operation corresponding to the position selected on the input panel.

The touch panel may be installed on the same plane as a control panel in which one or more of a keyboard, a switch, and a track ball are installed.

The graphic control unit may adjust one or more of position, size, and rotation of the input panel displayed within the display in response to a selection from a user.

Another embodiment of the present disclosure provides a graphic environment control device for controlling graphic environment displayed on a display of an ultrasonic diagnostic apparatus, including: an input panel layout display unit for displaying an input panel layout corresponding to a touch panel on the display; a touch position calculation unit for calculating a touch position corresponding to a touch on the touch panel; a screen position determining unit for determining a position corresponding to a calculated touch position within the input panel layout; and a control execution unit for executing a control function corresponding to a determined position.

The graphic environment control device may further include an input display unit for indicating on the display that the position is determined.

The input panel layout display unit may display selection menus for a plurality of different varieties of the input panel layout, and displays an input panel layout corresponding to a menu selected by a user from among the displayed selection menus.

The input panel layout display unit may display selection menus for one or more of position adjustment, size adjustment, and rotation adjustment of the input panel layout, and display the input panel layout with one or more of position, size and rotation adjusted in response to a selected menu from among displayed selection menus by a user.

Yet another embodiment of the present disclosure provides a graphic environment control method for controlling graphic environment displayed on a display of an ultrasonic diagnostic apparatus, including: displaying an input panel layout corresponding to a touch panel on the display; calculating a touch position corresponding to a touch detected on the touch panel; determining a position corresponding to a calculated touch position within the input panel layout; and executing a control function corresponding to a determined position.

The graphic environment control method may further include indicating the determined position on the display.

The process of displaying the input panel layout may includes displaying selection menus for a plurality of different varieties of the input panel layout, and displaying an input panel layout corresponding to a selected menu from among the displayed selection menus by a user.

The process of displaying the input panel layout may include displaying selection menus for one or more of position adjustment, size adjustment, and rotation adjustment of the input panel layout, and displaying the input panel layout with one or more of position, size and rotation adjusted in response to a selected menu from among the displayed selection menus by a user.

Advantageous Effects

According to the present disclosure as described above, an operator is relieved from the need to move arm positions between the control panel and touch screen for each manipulation of the ultrasonic diagnostic apparatus as well as the need for constant visual attention switches between the touch screen and display and thereby the operator's convenience is enhanced with the ultrasonic diagnostic apparatus.

DETAILED DESCRIPTION

Figure 1:
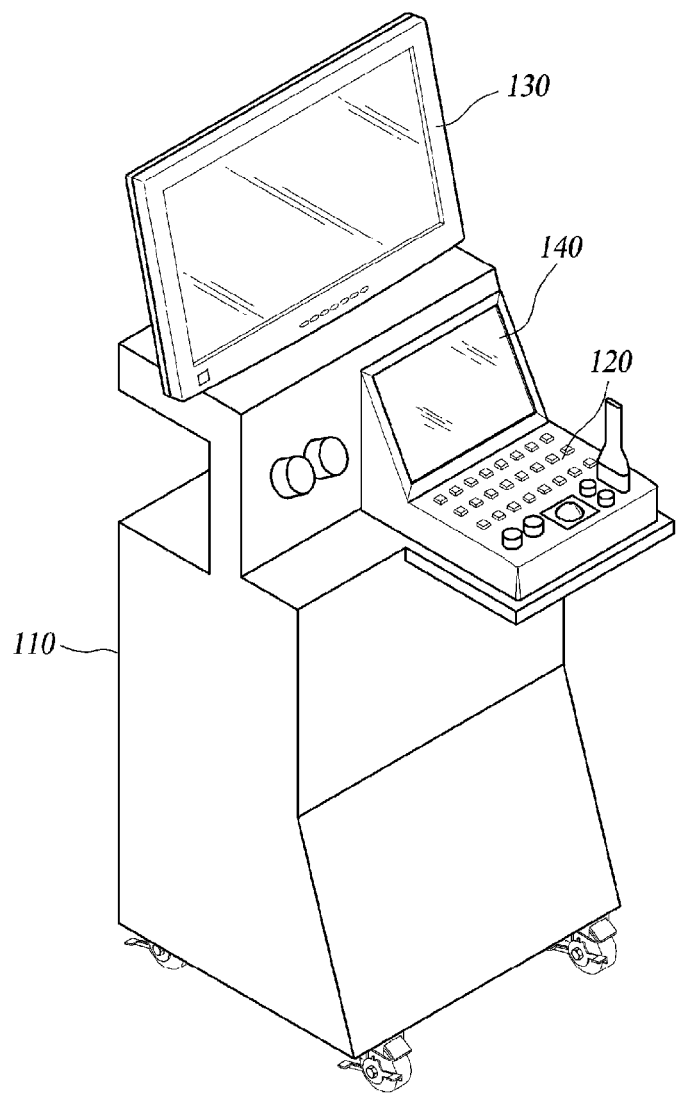
FIG. 1 is a diagram showing one example of a conventional ultrasonic diagnostic apparatus.
Figure 2:
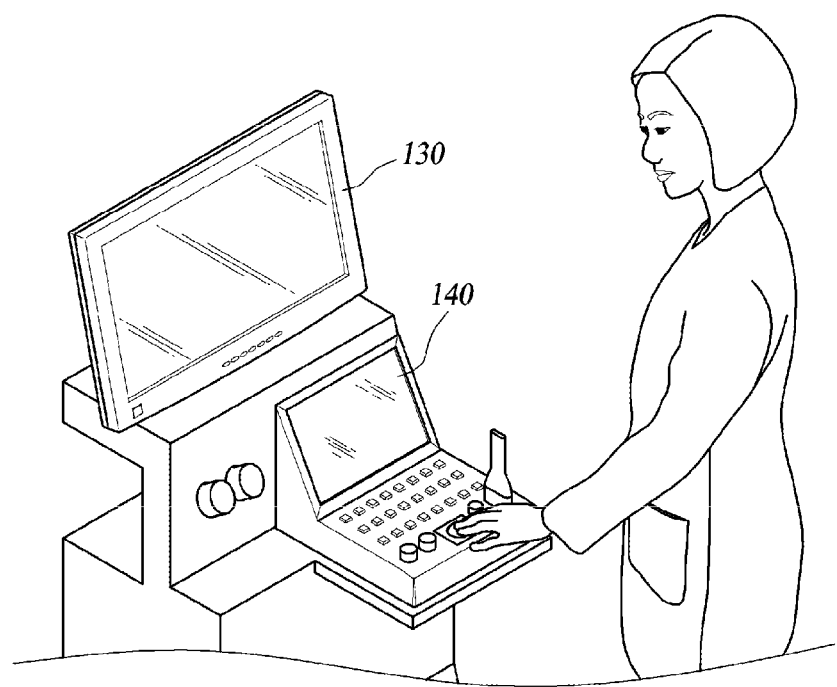
FIG. 2 is a diagram for describing a touch screen of FIG. 1.

Hereinafter, embodiments of the present disclosure will be described in detail with reference to the accompanying drawings. In the following description, like reference numerals designate like elements although they are shown in different drawings. Further, in the following description of the present embodiments, a detailed description of known functions and configurations incorporated herein will be omitted for the purpose of clarity.

Additionally, in describing the components of the present disclosure, there may be terms used like first, second, A, B, (a), and (b). These are solely for the purpose of differentiating one component from the other but not to imply or suggest the substances, order or sequence of the components. If a component were described as 'connected', 'coupled', or 'linked' to another component, they may mean the components are not only directly 'connected', 'coupled', or 'linked' but also are indirectly 'connected', 'coupled', or 'linked' via a third component.

Figure 3:
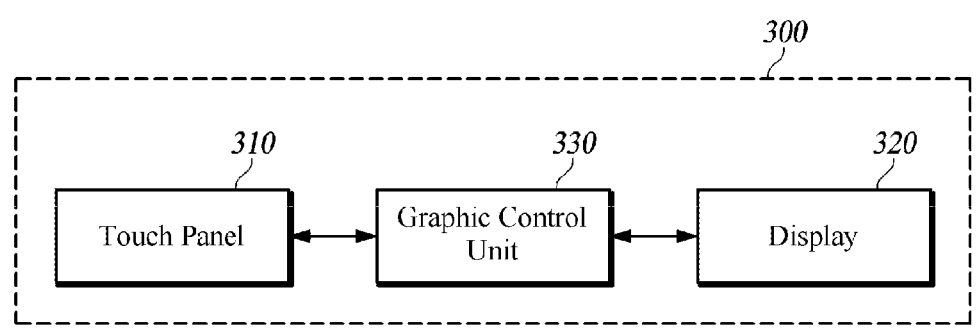
FIG. 3 is a schematic diagram showing a configuration of an ultrasonic diagnostic apparatus according to an embodiment of the present disclosure.

FIG. 3 is a schematic diagram showing a configuration of an ultrasonic diagnostic apparatus according to an embodiment of the present disclosure. Referring to FIG. 3, the ultrasonic diagnostic apparatus 300 according to the embodiment of the present disclosure includes a touch panel 310, a display 320, and a graphic control unit 330.

The touch panel 310 is an input device for detecting an operator touch position and includes a touch pad. The touch panel 310 used herein dispenses with a screen display function as an output device, and is conceptually different from a touch screen having a screen display function. Therefore, the touch panel 310 need not consider the angle of the line of sight of the operator, and may be installed on the same plane as the control panel 120 (see FIG. 1) in which one or more of a keyboard, a switch, and a track ball are installed. Since the touch panel and touch pad used in the embodiment of the present disclosure are conventionally available components, detailed description thereof will be omitted.

The display 320 displays images corresponding to an ultrasonic wave irradiated through a probe and an echo thereof.

The graphic control unit 330 displays an input panel layout corresponding to the touch panel 310 within the screen of the display 320, selects a point of the input panel correspondingly to a touch position detected through the touch panel 310, and performs control corresponding to the selected point of the input panel. In addition, the graphic control unit 330 may be configured to adjust one or more of the position, size, and rotation of the input panel displayed within the screen of the display 320 according to an operator's selection. The configuration and operation of the graphic control unit 330 may be realized by a graphic environment control device 400 of FIG. 4.

Figure 4:
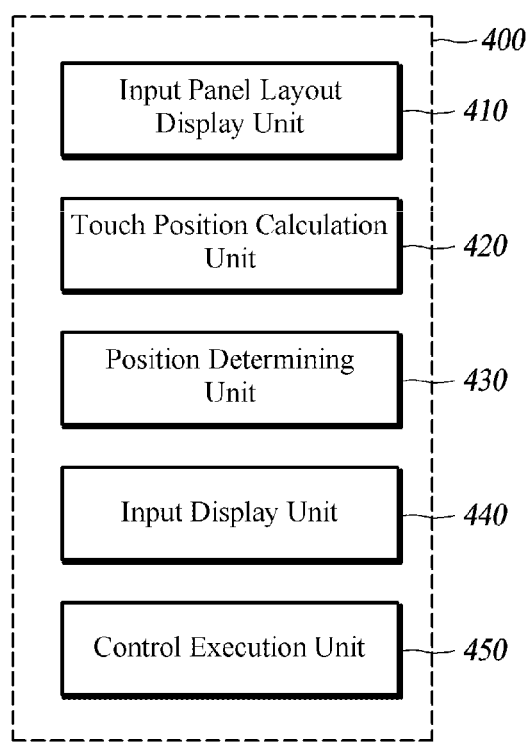
FIG. 4 is a schematic diagram showing one example of a graphic environment control device according to an embodiment of the present disclosure.

FIG. 4 is a schematic diagram showing one example of a graphic environment control device according to an embodiment of the present disclosure. The graphic environment control device 400 may operate as the graphic control unit 330 of FIG. 3. For this purpose, the graphic environment control device 400 may include an input panel layout display 410, a touch position calculation unit 420, a position determining unit 430, an input display unit 440, and a control execution unit 450.

The input panel layout display unit 410 displays the input panel layout corresponding to the touch panel 310 on the display 320. In addition, the input panel layout display unit 410 may include a plurality of different varieties of the input panel layout. In this case, the input panel layout display unit 410 may display a selection menu for each input panel layout on the display 320, and display an input panel layout corresponding to a menu selected by the operator on the display 320. The plurality of input panel layouts may be provided with representations of displayed input panels corresponding to each of the various functions when input and manipulation are performed on the functions by using the touch panel 310.

In addition, the input panel layout display unit 410 may display a selection menu for one or more of position adjustment, size adjustment, and rotation adjustment of the input panel, and display one or more of the adjusted position, size and rotation of the input panel corresponding to a menu selected by the operator.

The touch position calculation unit 420 calculates a touch position corresponding to an operator's touch with the touch panel 310. The method for calculating the touch position corresponding to the touch with the touch panel 310 adopts a known technique, and detailed description thereof will be omitted.

The position determining unit 430 determines a position corresponding to the touch position calculated by the touch position calculation unit 420 in the input panel layout. In this case, when the operator shifts the touch position across the touch panel 310, an arrow or cursor is adapted to follow suit thereafter in the input panel layout on the display 320. When the operator double-clicks the touch panel 310 at the touch position, its corresponding position may be recognized as determined.

When the position corresponding to the touch position is selected by the position determining unit 430, the input display unit 440 may indicate the selection of the position on the display 320. For example, when the operator double-clicks the touch panel 310 at the touch position while watching the position displayed on the display 320, the input display unit 440 may indicate the selection of the position by expressing the position in a distinctive color. The above-described displaying method of the input display unit 440 is merely exemplary, and various modifications may be made to the displaying method.

The control execution unit 450 executes a control function corresponding to the determined position. For this purpose, the control execution unit 450 may store different functions matchingly with each position of the input panel layout, and execute a function corresponding to the position selected by the position determining unit 430.

Figure 5:
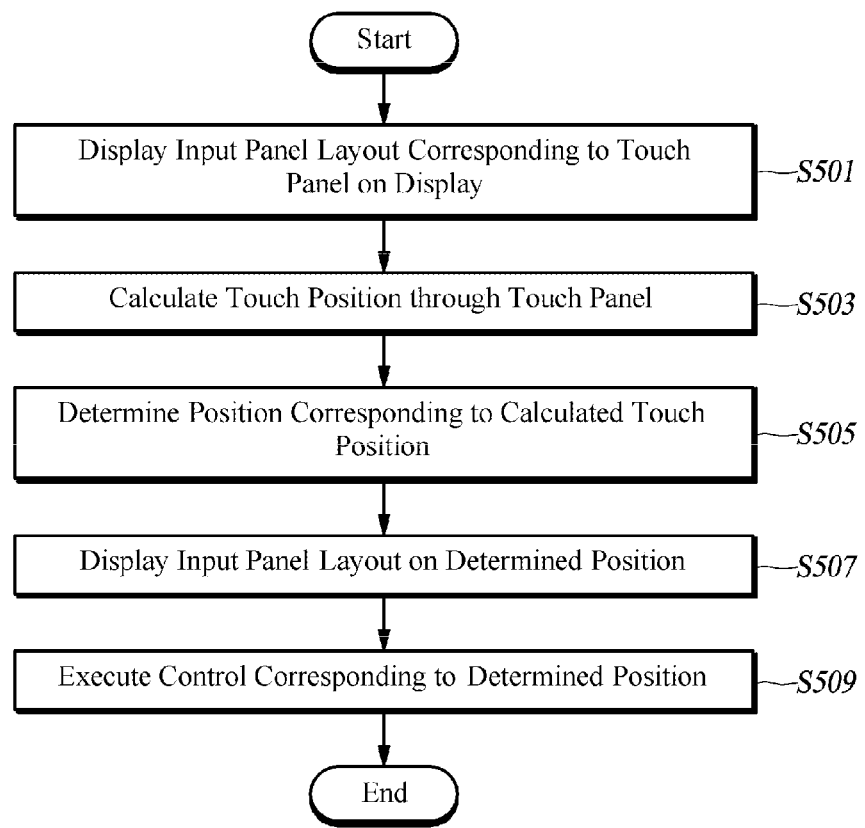
FIG. 5 is a flow diagram showing a graphic environment control method that is performed by the graphic environment control device of FIG. 4.

FIG. 5 is a flow diagram showing a graphic environment control method that is performed by the graphic environment control device of FIG. 4. The function and operation of the graphic environment control device 400 according to the embodiment of the present disclosure will be described in detail with reference to FIG. 5.

Figure 6:
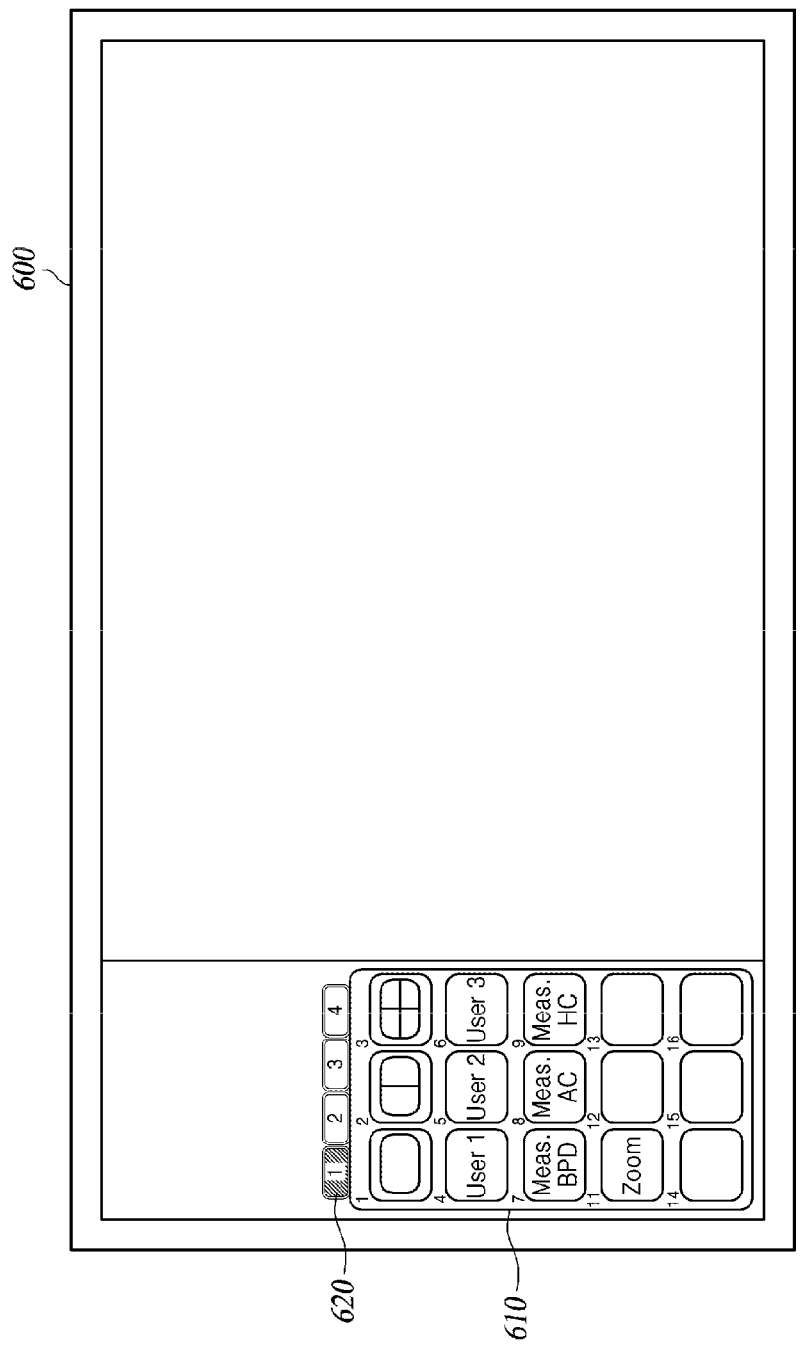
FIG. 6 is a diagram showing one example of a display screen that is realized by the graphic environment control device of FIG. 4.

As shown in FIG. 6, the input panel layout display unit 410 displays an input panel layout 610 corresponding to the touch panel 310 on a screen 600 of the display 320 (S501). The input panel layout display unit 410 may include a plurality of input panel layouts divided by functions, display selection menus 620 for the input panel layouts on the display 320, and display an input panel layout corresponding to a menu, selected by the operator among the displayed selection menus, on the display 320. FIG. 6 shows a case where an input panel layout corresponding to a selection menu 1 is displayed among selection menus 1 to 4.

In addition, the input panel layout display unit 410 may display a selection menu for one or more of position adjustment, size adjustment, and rotation adjustment of the input panel, and display the input panel with one or more of the position, size and rotation adjusted corresponding to a menu selected by the operator. For example, the position of the input panel layout may be shifted by locating the position at the lateral side of the input panel layout 610 and dragging the lateral side in a vertical direction, or the size of the input panel may be adjusted by locating the position at the edge of the input panel layout 610 and dragging the edge in a diagonal direction. In addition, the input panel may be rotated by rotation in a state that the position is fixed in the input panel layout 610.

The touch position calculation unit 420 calculates a touch position corresponding to an operator's touch with the touch panel 310 (S503). The method for calculating the touch position corresponding to the touch with the touch panel 310 adopts prior art technique, and detailed description thereof will be omitted.

The position determining unit 430 determined in the input panel layout a position corresponding to the touch position calculated by the touch position calculation unit 420 (S505). In this case, when the operator shifts the touch position across the touch panel 310, an arrow or cursor is implemented to follow suit thereafter in the input panel layout on the display 320. When the operator double-clicks the touch position of the touch panel 310, the position corresponding to the touch position may be recognized as determined.

When the position corresponding to the touch position is determined by the position determining unit 430, the input display unit 440 may display the determination of the corresponding screen position on the display 320 (S507). For example, when the operator double-clicks the touch position of the touch panel 310 while watching the screen position displayed on the display 320, the input display unit 440 may display the determination of the position by expressing the position in a distinctive color.

The control execution unit 450 executes a control function corresponding to the determined position (S509). For this purpose, the control execution unit 450 may store different functions matchingly with each position of the input panel layout.

As described above, the touch panel can be installed on the same plane as the control panel. Therefore, by displaying the input panel layout on the display, the operator is relieved from the need to move between different tilt angles during the manipulation of the ultrasonic diagnostic apparatus as well as the need for constant visual attention switches between different displays.

In the description above, although all of the components of the embodiments of the present disclosure may have been explained as assembled or operatively connected as a unit, the present disclosure is not intended to limit itself to such embodiments. Rather, within the objective scope of the present disclosure, the respective components may be selectively and operatively combined in any numbers. Every one of the components may be also implemented by itself in hardware while the respective ones can be combined in part or as a whole selectively and implemented in a computer program having program modules for executing functions of the hardware equivalents. Codes or code segments to constitute such a program may be easily deduced by a person skilled in the art. The computer program may be stored in computer readable media, which in operation can realize the embodiments of the present disclosure. As the computer readable media, the candidates include magnetic recording media, optical recording media, and carrier wave media.

In addition, terms like 'include', 'comprise', and 'have' should be interpreted in default as inclusive or open rather than exclusive or closed unless expressly defined to the contrary. All the terms that are technical, scientific or otherwise agree with the meanings as understood by a person skilled in the art unless defined to the contrary. Common terms as found in dictionaries should be interpreted in the context of the related technical writings not too ideally or impractically unless the present disclosure expressly defines them so.

Although exemplary embodiments of the present disclosure have been described for illustrative purposes, those skilled in the art will appreciate that various modifications, additions and substitutions are possible, without departing from essential characteristics of the disclosure. Therefore, exemplary embodiments of the present disclosure have not been described for limiting purposes. Accordingly, the scope of the disclosure is not to be limited by the above embodiments but by the claims and the equivalents thereof.

CROSS-REFERENCE TO RELATED APPLICATION

If applicable, this application claims priority under 35 U.S.C. §119(a) of Patent Application No. 10-2010-0055906, filed on Jun. 14, 2010 in Korea, the entire content of which is incorporated herein by reference. In addition, this non-provisional application claims priority in countries, other than the U.S., with the same reason based on the Korean Patent Application, the entire content of which is hereby incorporated by reference.

The invention claimed is:

1. An ultrasonic diagnostic apparatus comprising:
a display unit including a display area divided into a main display area and a secondary display area;
a touch panel, spatially separated from the display unit, for detecting a touch position, wherein the touch panel is without a display screen; and
at least one processor configured to:
display images formed based on echo signals reflected from a subject corresponding to transmitted ultrasonic waves on the main display area of the display unit;
display an input panel layout on the secondary display area of the display unit, wherein the input panel layout includes a plurality of selectable objects, and positions on the input panel layout are matched to positions on the touch panel;
determine a position on the input panel layout that corresponds to the touch position detected by the touch panel; and
perform a control operation of the selectable object corresponding to a determined position on the input panel layout.

2. The ultrasonic diagnostic apparatus of claim 1, wherein the touch panel is installed on the same plane as a control panel in which one or more of a keyboard, a switch, and a track ball are installed.

3. The ultrasonic diagnostic apparatus of claim 1, wherein the control unit adjusts one or more of position, size, and rotation of the input panel layout displayed on the display unit in response to a selection from a user.

4. A graphic environment control device for controlling graphic environment displayed on a display unit of an ultrasonic diagnostic apparatus, the graphic environment control device comprising:
an input panel layout display unit for displaying an input panel layout on part of a display area of the display unit, the input panel layout including a plurality of selectable objects;
a touch position calculation unit for calculating a touch position corresponding to a touch on a touch panel, wherein the touch panel is spatially separated from the display unit and is without a display screen, and wherein positions on the touch panel are matched to positions on the input panel layout;
a screen position determining unit for determining a position on the input panel layout that corresponds to a calculated touch position; and
a control execution unit for executing a control function of the selectable object corresponding to a determined position.

5. The graphic environment control device of claim 4, further comprising an input display unit for indicating on the display unit that the position is determined.

6. The graphic environment control device of claim 4, wherein the input panel layout display unit displays selection menus for a plurality of different varieties of the input panel layout, and displays an input panel layout corresponding to a menu selected by a user from among displayed selection menus.

7. The graphic environment control device of claim 4, wherein the input panel layout display unit displays selection menus for one or more of position adjustment, size adjustment, and rotation adjustment of the input panel layout, and displays the input panel layout with one or more of position, size and rotation adjusted in response to a selected menu from among displayed selection menus by a user.

8. A graphic environment control method for controlling graphic environment displayed on a display unit of an ultrasonic diagnostic apparatus, the graphic environment control method comprising:
displaying an input panel layout on part of a display area of the display unit, the input panel layout including a plurality of selectable objects;
calculating a touch position corresponding to a touch detected on the touch panel, wherein the touch panel is spatially separated from the display unit and is without a display screen, and wherein positions on the touch panel are matched to positions on the input panel layout;
determining a position on the input panel layout that corresponds to a calculated touch position; and
executing a control function of the selectable object corresponding to a determined position.

9. The graphic environment control method of claim 8, further comprising indicating the determined position on the display unit.

10. The graphic environment control method of claim 8, wherein the process of displaying the input panel layout comprises displaying selection menus for a plurality of different varieties of the input panel layout, and displaying an input panel layout corresponding to a selected menu from among displayed selection menus by a user.

11. The graphic environment control method of claim 8, wherein the process of displaying the input panel layout comprises displaying selection menus for one or more of position adjustment, size adjustment, and rotation adjustment of the input panel layout, and displaying the input panel layout with one or more of position, size and rotation adjusted in response to a selected menu from among displayed selection menus by a user.

* * * * *